(12) United States Patent
Townshend et al.

(10) Patent No.: US 11,293,020 B2
(45) Date of Patent: Apr. 5, 2022

(54) MOLECULAR SENSOR SELECTION

(71) Applicant: The Board of Trustees of the Leland Stanford Junior University, Stanford, CA (US)

(72) Inventors: Brent Townshend, Menlo Park, CA (US); Christina D. Smolke, Menlo Park, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 113 days.

(21) Appl. No.: 16/884,941

(22) Filed: May 27, 2020

(65) Prior Publication Data

US 2020/0362333 A1    Nov. 19, 2020

Related U.S. Application Data

(63) Continuation of application No. 15/744,718, filed as application No. PCT/US2016/039890 on Jun. 28, 2016, now Pat. No. 10,689,642.

(60) Provisional application No. 62/196,164, filed on Jul. 23, 2015.

(51) Int. Cl.
| | |
|---|---|
| *C12Q 1/68* | (2018.01) |
| *C12N 15/10* | (2006.01) |
| *C12N 15/113* | (2010.01) |
| *C12N 15/115* | (2010.01) |

(52) U.S. Cl.
CPC ..... *C12N 15/1048* (2013.01); *C12N 15/1096* (2013.01); *C12N 15/113* (2013.01); *C12N 15/115* (2013.01); *C12N 2310/12* (2013.01); *C12N 2310/16* (2013.01); *C12N 2330/31* (2013.01)

(58) Field of Classification Search
CPC .......................................................... C12Q 1/68
USPC ........................................................... 435/6.1
See application file for complete search history.

(56) References Cited

U.S. PATENT DOCUMENTS

| | | | |
|---|---|---|---|
| 5,656,462 A | * | 8/1997 | Keller ..................... C12P 19/34 435/91.2 |
| 6,127,173 A | | 10/2000 | Eckstein et al. |
| 2007/0077571 A1 | | 4/2007 | Ellington et al. |
| 2011/0021361 A1 | | 1/2011 | Chetverin et al. |

(Continued)

FOREIGN PATENT DOCUMENTS

| | | |
|---|---|---|
| WO | WO 2014/088830 | 6/2014 |
| WO | WO 2017/030659 | 2/2017 |

OTHER PUBLICATIONS

Piganeau et al., "In vitro Selection of Allosteric Ribozymes: Theory and Experimental Validation", Journal of Molecular Biology, 2001, 312(5): 1177-1190.

(Continued)

*Primary Examiner* — Aaron A Priest
(74) *Attorney, Agent, or Firm* — James S. Keddie; Bozicevic, Field & Francis LLP

(57) ABSTRACT

Provided herein, among other things, is an automatable procedure that employs in vitro directed evolution to create DNA sequences that encode a ligand-responsive ribozyme and which, when transcribed, can control expression of genes they are coupled to. The method also allows creation of functional RNA sequences that bind target molecules, without requiring any modification or immobilization of the target.

7 Claims, 5 Drawing Sheets

Specification includes a Sequence Listing.

(56) References Cited

U.S. PATENT DOCUMENTS

2011/0059433 A1* 3/2011 Marc .................. B01D 61/18
  435/5
2018/0346973 A1* 12/2018 Barany ................ C12Q 1/6827

OTHER PUBLICATIONS

Kobori et al., "High-throughput assay and engineering of self-cleaving ribozymes by sequencing", Nucleic Acids Research, 2015, 43(13): e85, doi: 10.1093/nar/gkv265.

Dupont et al., "Charactererisation of aptamer-target interactions by branched selection and high-throughput sequencing of SELEX pools", Nucleic Acids Research, 2015, 43(21): e139, doi: 10.1093/nar/gkv700.

Cho et al., "Quantitative selection and parallel characterization of aptamers", PNAS, 2013, 110(46): 18460-18465.

Liang et al., "A high-throughput, quantitative cell-based screen for efficient tailoring of RNA device activity", Nucleic Acids Research, 2012, 40(20): e154, doi:10.1093/nar/gks636.

Townshend et al., "High-Throughput, Data-Rich Cellular RNA Device Engineering", Nat Methods., 2015, 12(10): 989-994. doi:10.1038/nmeth.3486.

Bartel et al., "Islation of New Ribozymes from a Large Pool of Random Sequences", Science, 1993, 261: 1411-1418.

Wilson et al., "In Vitro Selection of Functional Nucleic Acids", Annu. Rev. Biochem., 1999, 68: 611-647.

Martin et al., "RNA Synthesis by in Vitro Selected Ribozymes for Recreating an RNA World", Life, 2015, 5: 247-268.

Jijakli et al., "The in vitro selection world", Methods, 2016, 106: 3-13.

* cited by examiner

```
                          SEQUENCE LISTING

<160> NUMBER OF SEQ ID NOS: 7

<210> SEQ ID NO 1
<211> LENGTH: 11
<212> TYPE: DNA
<213> ORGANISM: Artificial Sequence.
<220> FEATURE:
<223> OTHER INFORMATION: Synthetic nucleic acid sequence.

<400> SEQUENCE: 1
aaacaaacaa a                                                            11

<210> SEQ ID NO 2
<211> LENGTH: 17
<212> TYPE: DNA
<213> ORGANISM: Artificial Sequence.
<220> FEATURE:
<223> OTHER INFORMATION: Synthetic nucleic acid sequence.

<400> SEQUENCE: 2
aaaaagaaaa ataaaaa                                                      17

<210> SEQ ID NO 3
<211> LENGTH: 24
<212> TYPE: DNA
<213> ORGANISM: Artificial Sequence.
<220> FEATURE:
<223> OTHER INFORMATION: Synthetic nucleic acid sequence.

<400> SEQUENCE: 3
aatttaatac gactcactat aggg                                              24

<210> SEQ ID NO 4
<211> LENGTH: 57
<212> TYPE: RNA
<213> ORGANISM: Artificial Sequence.
<220> FEATURE:
<223> OTHER INFORMATION: Synthetic nucleic acid sequence.
<220> FEATURE:
<221> NAME/KEY: misc_feature
<222> LOCATION: (13)..(22)
<223> OTHER INFORMATION: N can be any nucleotide.
<220> FEATURE:
<221> NAME/KEY: misc_feature
<222> LOCATION: (41)..(44)
<223> OTHER INFORMATION: N can be any nucleotide.

<400> SEQUENCE: 4
```

```
gcugucaccg gannnnnnnn nnuccggucu gaugagucca nnnngggacg aaacagc      57
```

<210> SEQ ID NO 5
<211> LENGTH: 57
<212> TYPE: RNA
<213> ORGANISM: Artificial Sequence.
<220> FEATURE:
<223> OTHER INFORMATION: Synthetic nucleic acid sequence.
<220> FEATURE:
<221> NAME/KEY: misc_feature
<222> LOCATION: (13)..(16)
<223> OTHER INFORMATION: N can be any nucleotide.
<220> FEATURE:
<221> NAME/KEY: misc_feature
<222> LOCATION: (35)..(44)
<223> OTHER INFORMATION: N can be any nucleotide.

<400> SEQUENCE: 5

```
gcugucaccg gannnnuccg gucugaugag uccannnnnn nnnngggacg aaacagc      57
```

<210> SEQ ID NO 6
<211> LENGTH: 188
<212> TYPE: DNA
<213> ORGANISM: Artificial Sequence.
<220> FEATURE:
<223> OTHER INFORMATION: Synthetic nucleic acid sequence.
<220> FEATURE:
<221> NAME/KEY: misc_feature
<222> LOCATION: (1)..(1)
<223> OTHER INFORMATION: This residue may have a 5' biotin group
      modification followed by an 18-atom hexa-ethyleneglycol spacer.
<220> FEATURE:
<221> NAME/KEY: misc_feature
<222> LOCATION: (74)..(75)
<223> OTHER INFORMATION: An 18-atom hexa-ethyleneglycol spacer may be
      present between these two residues.

<400> SEQUENCE: 6

```
aatttaatac gactcactat agggcggaaa tttcaaaggt gcttcgctgt caccggatcc      60
ggtctgatga guccttttta tttttctttt tgctgtttcg tcctcacgga ctcatcagac     120
cggaaagcac atccggtgac agcgaagcac ctttgaaatt tccgccctat agtgagtcgt     180
attaaatt                                                             188
```

<210> SEQ ID NO 7
<211> LENGTH: 167
<212> TYPE: DNA
<213> ORGANISM: Artificial Sequence.
<220> FEATURE:
<223> OTHER INFORMATION: Synthetic nucleic acid sequence.
<220> FEATURE:
<221> NAME/KEY: misc_feature
<222> LOCATION: (1)..(1)
<223> OTHER INFORMATION: This residue may have a 5' biotin group
      modification followed by an 18-atom hexa-ethyleneglycol spacer.
<220> FEATURE:
<221> NAME/KEY: misc_feature
<222> LOCATION: (51)..(52)
<223> OTHER INFORMATION: An 18-atom hexa-ethyleneglycol spacer may be
      present between these two residues.
<220> FEATURE:

```
<221> NAME/KEY: misc_feature
<222> LOCATION: (74)..(75)
<223> OTHER INFORMATION: An 18-atom hexa-ethyleneglycol spacer may be
      present between these two residues.

<400> SEQUENCE: 7
aatttaatac gactcactat agggcggaaa tttcaaaggt gcttcgctgt caccggatcc      60
ggtctgatga gucctttta tttttctttt tgctgtttcg tcctcacgga ctcatcagac     120
cggaaagcac atccggtgac agcgaagcac ctttgaaatt tccgccc                  167
```

MOLECULAR SENSOR SELECTION

CROSS-REFERENCING

This application is a continuation of U.S. application Ser. No. 15/744,718, filed on Jan. 12, 2018, which is a § 371 national phase of International Application No. PCT/US2016/039890, filed on Jun. 28, 2016, which claims the benefit of U.S. Provisional Pat. App. Ser. No. 62/196,164, filed on Jul. 23, 2015, which applications are incorporated by reference herein.

GOVERNMENT SUPPORT

This invention was made with Government support under contract HR0011-11-2-0002 awarded by the Defense Advanced Research Projects Agency and under contract AT007886 awarded by the National Institutes of Health. The Government has certain rights in the invention.

BACKGROUND

It is well-known that the expression of genes can be modulated by the effects of the DNA sequence surrounding the gene. One such method is the insertion of a sequence which, when transcribed to RNA, forms a self-cleaving ribozyme (see, e.g., Prody et al Science 231: 1577-1580 (1986)).

Programmable RNA-based gene-regulatory devices have been designed with functional RNA parts that encode sensing, information transmitting, and actuating functions (Win et al *Proc. Natl. Acad. Sci.* 2007 104: 14283-8). RNA device architectures functionally connect sensor and actuator components, such that sensor-detected information is transmitted into controlled activity of the actuator domain. One class of RNA devices utilizes a hammerhead ribozyme (HHRz) actuator to modulate the stability of a target transcript through conditional control of ribozyme cleavage activity via binding of the cognate ligand. The ribozyme-based device framework supports the design of robust genetic controllers in different organisms, responsive to diverse ligands, exhibiting complex computation, and applied to regulate complex phenotypes. Typical design strategies link sensor and actuator components through a rationally designed or screened transmitter component that guides secondary structure conformation changes of the functional components.

However, these methods require a sensor that not only detects the molecule of interest but also functions correctly in the context of the device, effectively converting the concentrations of the molecules into control of the actuator domain. Existing work in finding aptamers that function as sensors typically use aptamers found using methods based on binding. These do not provide the sensor in the context of the device and often require chemical modifications of the target of interest. Other techniques that use a SELEX-based process to find aptamers that function as sensors in the context of an otherwise fixed ribozyme-based device, such as "allosteric selection" (Koizumi et al *Nat. Struct. Biol.* 1999 6: 1062-1071; Soukup et al, *J. Mol. Biol.* 2000 298: 623-632), have had limited success and require labor-intensive steps in each round that are not amenable to automation. Coupled with the need for many rounds of selection to isolate desirable sensor sequences from undesired amplicons, prior processes have limited practical utility.

SUMMARY

A method for selecting a ligand-responsive ribozyme is provided. In some embodiments, the method may comprise: in vitro transcribing a DNA library to produce RNA; reverse transcribing the RNA to cDNA; selectively amplifying the cDNA such that cDNA molecules corresponding to RNA molecules that have been cleaved are amplified by a different amount relative to cDNA molecules corresponding to uncleaved RNA; preparing the amplified cDNA for in vitro transcription; repeating the prior steps one or more times; and determining the sequence of one or more of the molecules in the product.

In contrast to other methods, practicing the present method does not require immobilization of the target molecules, which can be advantageous in certain circumstances. For example, existing selection methods require chemical modification and/or immobilization of small-molecule targets, which make those methods difficult to implement and limits the target molecule that can be used. Further, the use of unmodified target molecule removes issues with modifications affecting binding, which otherwise can result in finding aptamers that bind to the modified target but not the desired unmodified one, or an inability to find any aptamers that bind to the modified target. The present method does not require an understanding of the structure of the target molecule or even its identity. Further, if desired, one can perform counterselection steps against other molecules or mixtures of molecules. For example, one can perform differential selection against a target molecule to produce ribozymes that are not sensitive to other similar molecules. By including the similar molecules in the negative-target conditions, ribozymes that are sensitive to those molecules can be selected against. Further, one can perform a differential selection against complex mixtures. By executing the positive and negative cycles in two different mixtures, ribozymes can be obtained which are sensitive to one or more differences in the mixtures. This can be achieved without needing to predetermine which component(s) of the mixtures are sensed. Finally, the method can provide a switch in the context of an aptamer. Since the switch and aptamer are selected jointly, the resulting RNA device will be functional under the conditions of selection, and likely under other conditions.

The steps of many embodiments of the present method can be automated using a liquid-handling robot, if desired, making it possible to do several selections in parallel and to perform multiple rounds of selection within a few days, without human intervention. Finally, unlike many other aptamer selection methods, the present method can in some cases be implemented using very small amounts of target molecule and can be scaled down to low volumes, limited only by the need to retain adequate diversity during each cycle.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
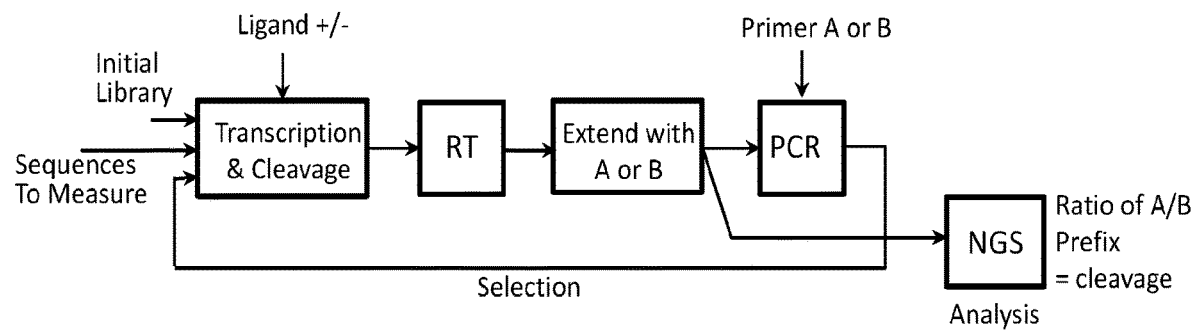
FIG. 1 is a flow-chart showing some of the steps of the present selection method.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides, ribonucleotides or a combination thereof, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds.

As used herein, the term "oligonucleotide" refers to a multimer of at least 10, e.g., at least 15 or at least 30 nucleotides. In some embodiments, an oligonucleotide may be in the range of 15-200 nucleotides in length, or more.

As used herein, the term "ligand-responsive" refers to an activity that changes (i.e., increases or decreases) in the presence of a ligand. A change may be decrease of at least 50%, at least 80%, at least 90% or at least 95%, or more, or an increase of at least 2-fold, at least 5-fold, at least 10-fold or at least 50-fold, or more.

Figure 4:
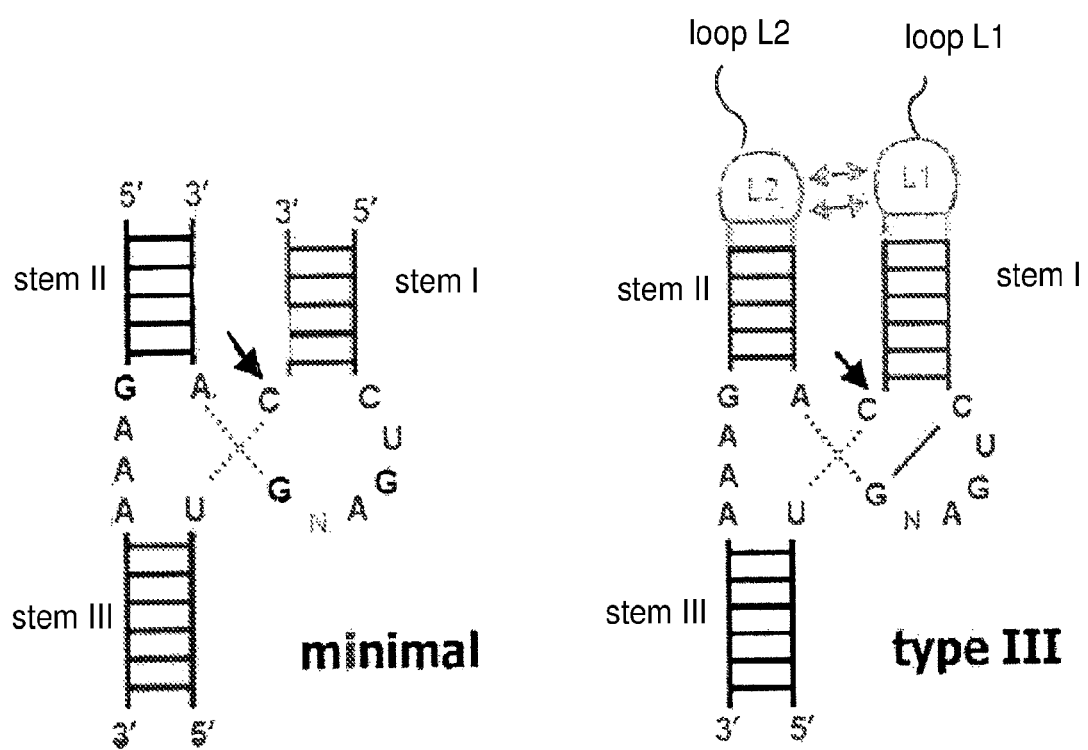
FIG. 4 schematically illustrates the structure of an exemplary ribozyme and a type III ribozyme.

As used herein, the term "ribozyme" refers to a RNA molecule motif that catalyzes cleavage and/or joining reactions at a specific site within an RNA molecule. The minimal hammerhead ribozyme is composed of three base paired stems (or "helices"), separated by short linkers of conserved sequence as shown in the crystal structure described in Scott (Cell 1995 81: 991-1002). These stems are called stems I, II and III. The conserved uridine-turn links stem I to stem II and usually contains the sequence CUGA. Stems II and III are linked by a sequence GAA. The cleavage reaction occurs between stem III and I, and is usually immediately 3' of a C. The structure-function relationships in ribozymes have been extensively reviewed (see, e.g., Hammann et al, RNA 2012 18: 871-885). The structure of an exemplary minimal hammerhead ribozyme and a type III ribozyme are shown in FIG. 4. The various parts of a hammerhead ribozyme, e.g., stem I, stem II, stem III, loop L1 and loop L2, etc. are defined with reference to FIG. 4. A ribozyme can contain one or more non-naturally occurring nucleotides, as described above.

As used herein, the term "RNA atamer" refers to a single-stranded RNA sequence that can specifically bind to a target molecule (a "ligand") with high affinity. The ligand for an aptamer can be any molecule or group of molecules; a polypeptide, or a small, non-proteinaceous organic molecule of less than 1 kDa. (e.g., less then 500 Da), for example. A limited number of aptamers that bind to a specific target molecule are known (see, e.g., Hernandez, et al, Curr Top Med Chem. 2015 15:1066-81, Darmostuk et al, Biotechnol Adv. 2015 S0734-9750 and Kang Adv. Biochem. Eng. Biotechnol. 2013 131: 153-69). Aptamers can bind a wide variety of exemplary ligands, including, without limitation, small molecules, such as drugs, metabolites, intermediates, cofactors, transition state analogs, ions, metals, nucleic acids, polysaccharides, glycoproteins, hormones, receptors, cell surfaces (such as cell walls and cell membranes), and toxins. In particular embodiments, an aptamer may be at least 15, at least 20, at least 25 or at least 30 nucleotides and up to 50, 70 or 100 nucleotides in length.

As used herein, the term "modified sequence" refers to a sequence that is not naturally occurring, i.e., not wild-type. For example, if a loop of a ribozyme has a modified sequence, then that loop has a sequence that is not found in the same loop of a wild type ribozyme.

As used herein, the term "autocatalytic cleavage" refers to a reaction in which a ribozyme catalyzes its own cleavage.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "optically detectable protein" refers to a protein whose expression can be detected by the presence of an optical signal produced by the protein. An optical signal is produced by a protein, for example, when the protein is capable of being excited by a particular wavelength of light and emits another wavelength of light which is detectable. An optical signal is produced by a protein, for example, when the protein catalyzes a reaction which results in a light signal. Fluorescent proteins, luminescent proteins, etc., are examples of optically detectable proteins.

The term "expression cassette" refers to a nucleic acid sequence comprising a promoter region, a coding sequence, and, optionally, a 3' untranslated region (UTR).

The term "splint oligonucleotide", as used herein, refers to an oligonucleotide that, when hybridized to other polynucleotides, acts as a "splint" to position the polynucleotides next to one another so that they can be ligated together using, e.g., T4 DNA ligase or another ligase.

Other definitions of terms may appear throughout the specification.

DETAILED DESCRIPTION

As noted above, a method for selecting a ligand-responsive ribozyme is provided. In certain embodiments, the method may comprise: (a) in vitro transcribing a DNA library to produce RNA; (b) reverse transcribing the RNA to cDNA; (c) selectively amplifying the cDNA such that cDNA molecules corresponding to RNA molecules that have been cleaved are amplified by a different amount relative to cDNA molecules corresponding to uncleaved RNA; (d) preparing the amplified cDNA of (c) for in vitro transcription; (e) repeating steps (a)-(d) one or more times; and, (f) determining the sequence of one or more of the molecules in the product of step (e).

Step (a) of the method can be done in the presence or absence of a target molecule (a prospective ligand). As such, the repeats of steps (a)-(d) may alternate between repeats in which step (a) is done in the presence of the target molecule and repeats in which step (a) is done in the absence of the target molecule, thereby allowing one to select for sequences that encode ribozymes that are autocatalytically active only in the presence of the ligand or ribozymes that are autocatalytically inactive only in the presence of the ligand.

For example, in performing steps (a)-(d) for the first time, sequences that encode ribozymes that are not catalytically active in the presence of the target molecule can be selected, and in the next round sequences that encode ribozymes that are catalytically active in the absence of the target molecule can be selected. Repeating these steps will result in selection of a ribozyme that is catalytically active in the absence of the target molecule but not the presence of the target molecule. Along similar lines, in performing steps (a)-(d) for the first time, sequences that encode ribozymes that are not catalytically active in the absence of the target molecule can be selected, and in the next round sequences that encode ribozymes that are catalytically active in the presence of the target molecule can be selected. Repeating these steps will result in selection of a ribozyme that is catalytically active in the presence of the target molecule but not the absence of the target molecule.

In some embodiments, the selective amplifying step (c) can be done by polymerase chain reaction (PCR), which selectively amplifies either the cDNA molecules corresponding to RNA molecules that have been cleaved or the cDNA molecules that correspond to uncleaved RNA, relative to one another. After steps (a)-(d) have been repeated one or more times (e.g., at least 5 or at least 10 times, as desired) sequences encoding ligand-responsive ribozymes that have a desired activity (e.g., ribozymes are catalytically active only in the presence or in the absence of a ligand) are highly enriched in the sample and can be identified by sequencing.

In some embodiments, the selective amplifying of step (c) may comprise ligating a prefix oligonucleotide to either the cDNA molecules corresponding to RNA molecules that have been cleaved or the cDNA molecules that correspond to uncleaved RNA, as desired. In some embodiments, a prefix oligonucleotide comprising an RNA polymerase promoter and a sequence encoding a non-variable part of the ribozyme that is 5' of the cleavage site may be ligated to cDNA molecules that encode RNAs that are cleaved in the presence or absence of a target molecule, thereby allowing one to selectively amplify those cDNAs and re-transcribe them for further selection. In other embodiments, a prefix oligonucleotide comprising an RNA polymerase promoter may be ligated to cDNA molecules that encode RNAs that are not cleaved in the presence or absence of a target molecule, thereby allowing one to selectively amplify those cDNAs and re-transcribe them for further selection. In either embodiment, the ligating may be done by using a splint oligonucleotide that splints the joint between the prefix oligonucleotide and the cDNA.

As alluded to above, the in vitro transcribing step (a) may be performed in either the presence of or absence of a target molecule, e.g., a small molecule, thereby providing a way by which sequences that encode ribozymes that only cleave in the presence of the target molecule and sequences that encode ribozymes that only cleave in the absence of the target molecule can be selected. In some embodiments, the in vitro transcribing step (a) may be performed in the presence of a mixture of target molecules. In these embodiments, in some cases, the target molecules may differ during each repeat of steps (a)-(d).

In some cases, there may be two target molecules (or mixtures of target molecules). In these embodiments: i. the in vitro transcribing step of some repeats of steps (a)-(d) may be done in the presence of the first target molecule, and the selective amplifying step of those repeats may comprise amplifying cDNA corresponding to cleaved RNA and ii. the in vitro transcribing step of the other repeats of steps (a)-(d) may be done in the presence of the second target molecule, and the selective amplifying step of those repeats may comprise amplifying cDNA corresponding to uncleaved RNA.

In some embodiments, steps (a)-(e), may be implemented using a liquid-handling robot. The determining step (f) may be done using high-throughput, e.g., next generation, sequencing. In these embodiments, the cDNAs may be amplified using forward and reverse primers that are compatible with a selected next generation sequencing platform, and then sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, methods for library preparation, reagents, and final products for each of the steps.

The sequence reads identified from this step can then be examined to identify sequences that have been selected by the method. These sequences can then be re-synthesized and tested.

In some embodiments, the target molecule (i.e., the ligand) may be a non-proteinaceous compound that has a molecular weight in the range of 50 to 2,500 Da, e.g., less then 500 Da, less then 400 Da or less then 300 Da, for example. In certain cases, a ligand may be functionally inert relative to cells that contain a ribozyme, thereby allowing the ribozyme to be activated or inactivated in a cellular context without significantly affecting the cell. In other embodiments, the ligand may be produced by the cell that contains the ribozyme, e.g., as a metabolite.

Also provided is a method to isolate an RNA aptamer, comprising: (a) in vitro transcribing a DNA library to produce RNA; (b) reverse transcribing the RNA to cDNA; (c) selectively amplifying the cDNA such that cDNA molecules corresponding to RNA molecules that have been cleaved are amplified by a different amount relative to cDNA molecules corresponding to uncleaved RNA; (d) preparing the amplified cDNA of (c) for in vitro transcription; and, (e) repeating steps (a)-(d) one or more times; and, (f) determining the sequence of one or more of the molecules in the product of step (e).

In the example described below, the screening method may be implemented using a hammerhead ribozyme. In theory, however, the method may be implemented using any ribozyme, as long as the ribozyme is capable of autocatalytic cleavage and the ribozyme is cleaved into two parts, one part containing a fixed sequence (the sequence of which can be rejoined onto cDNA made from the other part to reconstitute the ribozyme) and the other part having one or two or more randomized sequences. In some embodiments, the ribozyme used may be a type III hammerhead ribozyme (meaning that there are covalently closed loops at the ends of both stem I and stem II), however the present results are believed to be directly applicable to type I and type II ribozymes (which have a similar structure to type III hammerhead ribozymes (see, e.g., Hammann et al, RNA 2012 18: 871-885)). The general features of a hammerhead ribozyme and a type III hammerhead ribozyme are schematically illustrated in FIG. 4.

Relative to a wild-type hammerhead ribozyme, the library members used in some embodiments of the method may have the catalytic core of a hammerhead ribozyme, a first loop that has been replaced by random sequence of 3-10 nt, e.g., 4-8 nt and a second loop that comprises at least 10 or at least 20, e.g., 25 to 75 or 30 to 60 randomized positions. The first and second loops are loops L1 and L2 respectively, or loops L2 and L1 respectively, meaning that if one of those loops is replaced by a random sequence of 3-10 nt, e.g., 4-8 nt, the other contains at least 10 or at least 20, e.g., 25 to 75 or 30 to 60 randomized positions. For example, in some cases, the first loop is loop L1 and the second loop is loop L2, and in other cases the first loop is loop L2 and the second loop is loop L1. In some embodiments, the ribozymes in the initial library may comprise a first stem (i.e., stem I) of 4-7 bp terminating in a loop (loop L1) of 4-100 nt, a second stem (i.e., stem II) of 4-6 bp terminating in a loop (loop L2) of 4-100 nt, and a third stem (stem III) of 3-6 bp, wherein: (i) the first and second stems are joined by sequence CUGANGA, (ii) the second and third stems are joined by sequence GAA, and (iii) the second and third stems are joined by a C, as illustrated in FIG. 4.

In some embodiments, any of the methods described above may comprise (a) incubating a population of candidate ribozymes under cleavage conditions, wherein the candidate ribozymes comprise the catalytic core of a ribozyme and are of the formula X-Y-Z (which may be 5' to 3' or 3' to 5'), wherein sequence X does not vary, Y is an autocatalytic cleavage site, and sequence Z comprises one or more regions of variable sequence; (b) making cDNA from the product of step (a); (c) selectively appending: i. an RNA polymerase promoter and ii. sequence X to the cDNA copies of cleavage products comprising sequence Z, made in step (b); (d) amplifying the products of step (c); (e) transcribing the product of step (d) to produce a second population of the candidate ribozymes of formula X-Y-Z, (f) repeating steps (a)-(d) one or more times on the product of (e); and (g) identifying an amplified sequence. Step (a) may be done in the presence of a target molecule and step (e) may be done in the absence of that molecule, or vice versa, as desired, to select for a ligand-responsive ribozyme.

Also provided herein is a method for selectively ligating a prefix oligonucleotide to cDNA, comprising: (a) combining i. the prefix oligonucleotide to be ligated to the cDNA, ii. a splint oligonucleotide whose 3' end is complementary to the 3' end of the cDNA and whose 5' end is complementary to the 5' end of the prefix oligonucleotide, and iii. a ligase to produce a ligation mix; and (b) incubating the ligation mix to ligate the prefix oligonucleotide to the cDNA. In some embodiments, the splint oligonucleotide has a chemical modification that prevents extension or ligation of its 3' end. In some embodiments, the prefix oligonucleotide may be 5' phosphorylated. In some embodiments, the cDNA is the reverse transcription product of an RNA that has undergone self-cleavage.

In some embodiments, this method may comprise: a) reverse transcribing a first autocleavage product of a ligand-responsive ribozyme to produce a DNA product; b) ligating an oligonucleotide encoding a second autocleavage product of the ligand-responsive ribozyme onto the DNA product using a splint oligonucleotide, to produce a ligation product;

and c) transcribing the ligation product, thereby producing a copy of the ligand-responsive ribozyme.

Some details of the method summarized above are provided below.

The embodiment of the method shown in FIG. 1 starts with an initial library of DNA that includes a T7 promoter followed by the sequence for the RNA device including spacers and degenerate regions. Transcription is carried out with or without the target ligand present and the resulting RNA has the opportunity to self-cleave during this time. The RNA products are then reverse-transcribed to cDNA. The 3' end of the cDNA corresponding to either the cleaved or uncleaved RNA is then ligated to a prefix oligonucleotide and subsequently only those prefixed molecules are amplified using PCR. The PCR product is then used as input to the subsequent round of the same steps.

Rounds of selection proceed with alternating positive and negative selections. Positive selections are achieved by performing the transcription/cleavage in the presence of the target(s) and then selectively ligating a prefix primer to the cDNA corresponding to uncleaved products. Negative selections have no target(s) present during transcription/cleavage and the ligation is performed selectively on cleaved products.

Following up to 40 or more cycles of selection, the evolved pool of DNA can be sequenced using any high-throughput sequencing method available such as Illumina-based sequencing. Functional switches will be enriched during the cycles of selection and will thus occur with higher frequency in the sequenced pools. The individual sequences can then be synthesized and tested using a variant of the same method. This analysis, also shown in FIG. 1, starts with the single sequence template and the same steps of cotranscription, reverse transcription, and ligation are performed, but in this case both the uncleaved and cleaved sequences are ligated separately. The relative abundance of the cleaved and uncleaved can then be measured using quantitative PCR (qPCR), sequencing, or any other method known to those in the field. The ratio of cleaved to uncleaved sequences gives a measure of the cleavage rate of that sequence under the conditions present during the transcription/cleavage test. This can be repeated under varying target concentrations to measure the performance of the device.

Each cycle of the process can be controlled through several mechanisms, which can affect the speed of convergence and the properties of the sequences in the final pool: concentration of the DNA used for transcription, the presence or absence of target(s) present during the transcription/cleavage step, the choice and concentration of the target(s) used, duration of the transcription/cleavage reaction, the buffer conditions during each step including, in particular, the free $Mg^{++}$ concentration, whether ligation following RT is done selectively onto the cDNA corresponding to the cleaved RNA products or onto the uncleaved RNA products, and the choice of ligation prefix.

The DNA library used in the initial step of the method may, in some embodiments, have a complexity of at least $10^9$, e.g., at least $10^{10}$, at least $10^{11}$, at least $10^{12}$ or at least $10^{13}$ and may comprise a plurality of DNA constructs each comprising a bacteriophage (e.g., T7 or T3) promoter operably linked to a coding sequence for a candidate ribozyme, where the candidate ribozyme comprises a catalytic core, a first loop (which can be L1 or L2) comprising a random sequence of 3-10 nt, e.g., 4-8 nt, and a second loop (which can be L1 if the first loop is L2 or L2 if the first loop is L1) comprising at least 10 or at least 20 nt, e.g., 25-75 nt or 30-60 nt in randomized positions. In some embodiments, the ribozymes encoded by the library may comprise a first stem (i.e., stem I) of 4-7 bp terminating in a loop (loop L1), a second stem (i.e., stem II) of 4-6 bp terminating in a loop (loop L2), and a third stem (stem III) of 3-6 bp, wherein: (i) the first and second stems are joined by sequence CUGANGA, (ii) the second and third stems are joined by sequence GAA, and (iii) the second and third stems are joined by a C, as illustrated in FIG. 4.

The individual steps in the above method are described in detail in the following sections.

Initial Library Design

Figure 2:
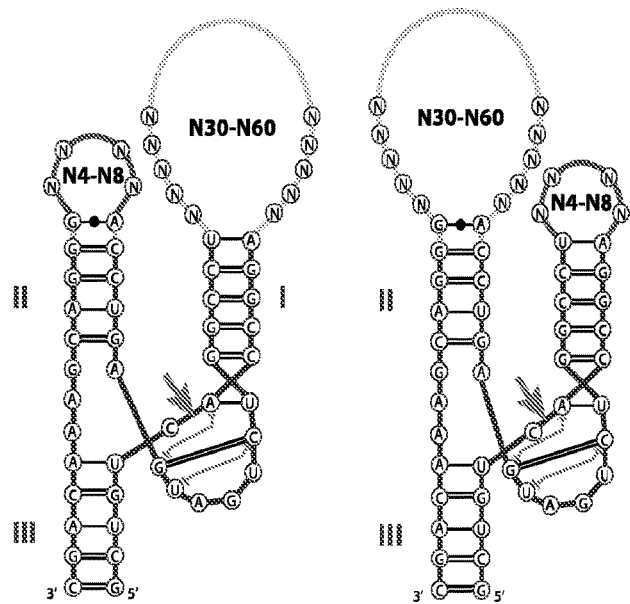
FIG. 2 shows an example of a library, shown with respect to the RNA sequence formed following transcription. Only the RNA device itself is shown; spacers, promoters, and other sequences that are prefixed or suffixed to the library are not shown in this figure. The RNA device on the left comprises a nucleic acid sequence as set forth in SEQ ID NO:4, and the RNA device on the right comprises a nucleic acid sequence as set forth in SEQ ID NO:5.

The initial library design can be any set of sequences that might encompass a functional ribozyme. However, since these are not known a priori, the library may contain a ribozyme core, such as the Hammerhead Ribozyme (HHRz), and a variable region which will be evolved to form the aptamer needed for the sensing of the target. In addition, other regions may be variable to allow solutions that require changes to other parts of the sequence. In the preferred embodiment, one loop (either loop I or loop II in FIG. 2) of the Hammerhead Ribozyme is replaced with a random region of 30-80 (e.g., about 60) degenerate nucleotides. The other loop is replaced with between 4 and 8 degenerate nucleotides with all lengths approximately equally probable.

The RNA device may be flanked with a spacer sequence designed to minimize interactions with other parts of the device or with other RNA that may be transcribed in the context of the device. In some embodiments, the spacer sequence at the 5' end comprises the sequence AAACAAACAAA (SEQ ID NO:1) and the sequence at the 3' end comprises AAAAAGAAAAATAAAAA (SEQ ID NO:2). In addition, a T7 promoter sequence, AATTTAATACGACTCACTATAGGG (SEQ ID NO:3), is added at the 5' end prior to the spacer to allow transcription by T7 RNA polymerase, though other sequences and/or polymerases can be used for this.

Library Synthesis

The library can be synthesized using any method of oligonucleotide synthesis known to those in the field. Degenerate nucleotides can be formed at any position using either machine-mixing of the nucleoside phosphoramidites, or, preferably with hand mixing as this provides more uniform randomization including compensation for unequal coupling efficiency for the bases. In one embodiment, the reverse-complement of the entire sequence of the library can be chemically synthesized and then annealed with a sequence complementary to the T7 promoter region of the oligonucleotide to allow runoff T7 transcription. In another embodiment, the entire sequence of the library can be chemically synthesized and then PCR amplified using primers matching the ends of the library sequence. In another embodiment, the library can be formed from 2 or more oligonucleotide components that are subsequently joined using any method known to those in the field, such as overlap-extend PCR.

Regardless of the method used to synthesize the initial library, enough molecules should be synthesized to obtain a desired level of diversity, e.g., $>10^{15}$ unique sequences, to maximize the probability that a functional device sequence will be contained within the initial library.

Cotranscription

Each cycle of the method begins with a DNA template, which can be the library described above, the product of a prior cycle, or a mixture of one or more sequences to be analyzed. This template is transcribed in vitro using a DNA-directed RNA polymerase, such as T7 RNA Polymerase. Once the RNA is synthesized, it can adopt the structure of an active ribozyme and may self-cleave during this stage. Thus, this stage consists of both transcription and the actual cleavage reaction that will ultimately be used to select certain sequences over others. The conditions under which the cotranscription occurs will affect this selection process. Specifically, the amount of free $Mg^{++}$ is known to both affect the rate of transcription and the cleavage rate of ribozymes. If the goal of the selection is to obtain RNA devices which will function in vivo, then it is preferable to adjust the buffer conditions to simulate the conditions that will be present during operation of the device in vivo. In particular, it is preferable to maintain the free $Mg^{++}$ levels to ones similar to those found in cells, typically less than 1 mM. This can be achieved either by adjusting the amount of $Mg^{++}$ added to the reaction or by addition of magnesium chelators such as EDTA or the nucleotide triphosphates used to synthesize the RNA.

The amount of time during which the cotranscription reaction occurs also controls the stringency of the selection. Shorter cotranscriptions will provide less time for cleavage to occur resulting in a lower fraction of the RNA molecules cleaved. This property can be used advantageously to adjust the stringency of selection during different cycles and to modify the selection during positive vs. negative selection cycles.

It also at this stage that the target molecule(s) can be added to the transcription mixture to achieve positive vs. negative selection. In one embodiment this may be a single species of molecule for which a sensor is desired. In another embodiment, this may be a mixture of molecules for which a sensor is desired. In addition, the "negative" selection cycles may include other molecules for which it is desired that the device does not respond. In this way, a device can be evolved that differentially responds to one set of conditions versus another set of conditions.

Following the chosen cotranscription time, the reaction can be stopped by addition of reagents known to arrest the transcription process. It also may be desirable to stop any additional cleavage from occurring. In the preferred embodiment, this is achieved by addition of EDTA such that most of the free $Mg^{++}$ is chelated, making it unavailable as a cofactor for the transcription or cleavage reactions. Also, in the preferred embodiment, an oligonucleotide is added that is complementary with the 3' end of the RNA, extending up to the degenerate region in helix II of the device. The annealing of this oligonucleotide serves two purposes: to prevent further cleavage by creating a stable RNA:DNA hybrid that disrupts the catalytically-active conformation of the device; and to act as a reverse-transcription primer for the next stage.

Note that the cotranscription stage, and all subsequent stages of the selection cycles, may involve only liquid-handling movements and incubations and are thus easily amenable to automation on a robotic platform.

Reverse Transcription

The reverse transcription stage synthesizes a DNA strand complementary to the RNA just transcribed. This can be achieved using any reverse transcription enzyme, e.g., Omniscript. This reaction is primed by a DNA oligonucleotide added following transcription. The process of reverse transcription is well-known to those in the field.

In some embodiments of the invention, one or more of the oligonucleotides used for the library or the reverse transcription may be modified to allow magnetic separation to be performed. For example, addition of a biotin label to the reverse transcription primer can allow the cDNA to be separated from other components using streptavidin-coated magnetic beads.

Ligation/Extension

Following reverse transcription, there should be two populations of cDNA of interest present; one consists of RNA that underwent cleavage subsequent to transcription and the other consists of RNA that did not cleave. The primary goal of each selection cycle is to differentially enrich one population over the other.

If the goal of the selection is to obtain RNA devices that undergo greater cleavage when the target is not present, then cycles where the target was added to the transcription mixture will be coupled with reactions at this stage that favor cDNA corresponding to uncleaved RNA, and cycles where the target was not added will be coupled with reactions at this stage that favor cDNA corresponding to cleaved RNA.

Figure 3:
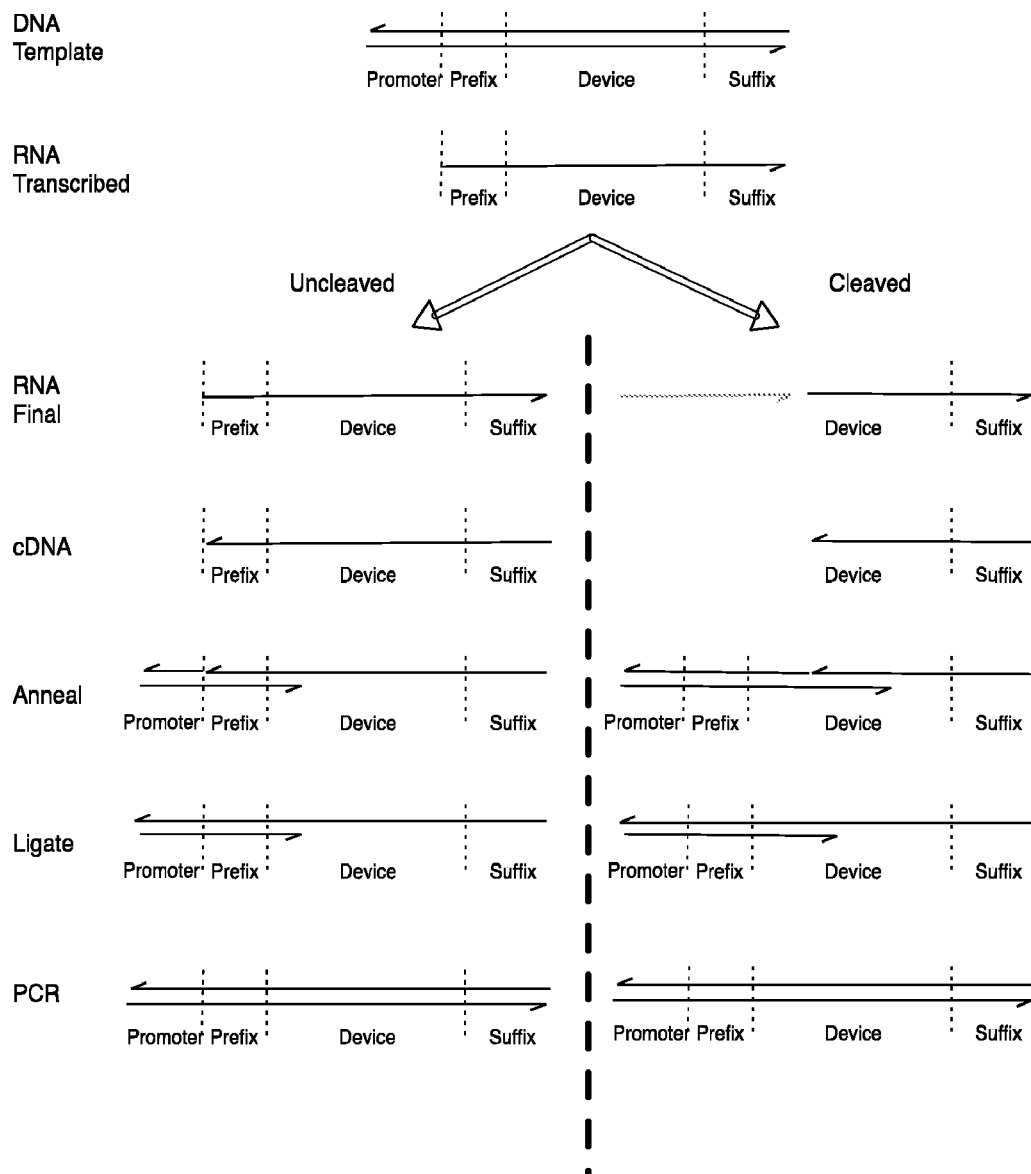
FIG. 3 shows one method used to ligate new prefixes onto the 3' of the cDNA produced by cleaved and uncleaved populations.

In one embodiment, as shown in FIG. 3, ligation of the cDNA with a prefix oligonucleotide can be used to mark one of the two populations in such a way that subsequent PCR reactions will differentially amplify this population. This can be achieved through use of a splint oligonucleotide along with the prefix oligonucleotide and a ligation enzyme such as T4 DNA Ligase (FIG. 3). A different pair of splint and extension oligonucleotides are used to extend the 3' end of the cDNA formed from the cleaved versus the uncleaved populations. In each case, the splint is complementary to both the prefix oligonucleotide (over the 5' nucleotides of the splint) and to the cDNA (over the 3' nucleotides of the split). The 3' end of the splint may be blocked against extension to prevent its extension during subsequent steps using a chemical modification during synthesis such as a C3 spacer or dideoxycytidine. The 5' end of the prefix oligonucleotide may be phosphorylated to allow it to be ligated to the cDNA. These pairs are designed such that they will place the 5' end of the extension oligonucleotide in close proximity to the 3' of either the cleaved or uncleaved cDNA allowing a ligation reaction to occur there preferentially.

Alternative means of enriching one population over the other are also possible. PCR amplification using primers complementary to the ends of the cDNA corresponding to uncleaved RNA can enrich this population. Alternatively, prefixes can be prepended to the cDNA using other methods such as PCR or Klenow extension.

For selection, one of either the cleaved or uncleaved populations will have the prefix ligated and this population can then be amplified in the subsequent stage, preparing it for the next cycle of enrichment. For analysis, the cDNA sample can be split and the two ligation reactions can be performed separately allowing the ratio of the two populations (cleaved and uncleaved) to be measured using qPCR or other methods.

PCR

The final stage of the selection process is an optional PCR amplification of the desired population to prepare it for the next cycle. This can be used to selectively amplify the population of interest and to add on the T7 promoter sequence. It also serves to increase the concentration of the cycle result to a level appropriate for the next round. This PCR can be done with any of the methods well known in the field, but preferably using an enzyme with high-processivity and low sequence-dependent bias, such as Kapa HiFi. To avoid production of chimeras and amplicons, the minimum number of PCR cycles necessary to achieve the needed amplification should be used.

For cycles where the unamplified product is at high enough concentration, the PCR step may be omitted and the splinted, ligated product can be used directly for T7 runoff transcription.

qPCR

After each cycle or set of cycles, the bulk cleavage of the pool can be measured using quantitative PCR. As described above, ligation of both the cleaved and uncleaved populations can be separately performed. The products of those ligations can be amplified using primer pairs that amplify only extended products, such as one complementary to the T7 promoter region and one matching the sequence of the last 20-24 nucleotides of the library, including the terminal spacer. By comparing the ratio of the measured concentrations of the two populations, the average cleavage of the pool can be determined. In this way cleavage of the pools from each cycle can be measured and tracked. This can be used as a stopping criterion for the method since a pool for which a significant fraction are functional devices will also show different levels of cleavage in the positive-target vs negative-target cycles.

Sequencing

At any point in the operation, e.g., after enough cycles have been run to significantly enrich desirable sequences as determined by bulk cleavage or other measures, the current pool can be sequenced to determine the primary sequence of potential RNA devices. In the preferred embodiment this is done by sequencing of the cDNA following co-transcription with and without target. The cDNA from each condition is used to form a library suitable for sequencing using well-known cDNA library preparation methods, barcoded with distinct sequencing adapters, and sequenced on a high-throughput sequencer such as an Illumina NextSeq. The reads so obtained can be aligned to the library and sequences can be counted in each condition and sub-tallied as to whether the sequence represents cDNA from uncleaved or from cleaved RNA. The ratio of these counts gives an estimate of the cleavage percentage in each of the conditions barcoded. Reference sequences can also be included to allow compensation for different amounts of amplification of the cleaved and uncleaved populations during the sequencing library preparation. Switch candidates are the sequences that show significantly different cleavage in the negative and positive target conditions. The statistical power of that test is dependent on the number of reads obtained for each sequence, which is in turn dependent on the degree of enrichment that the pool underwent prior to sequencing. If no switches are statistically significant, then additional selection rounds can be applied to further enrich the pool and the sequencing can be repeated. If the pool has been over-enriched and only a few sequences can be identified, then a sample of the pool from an earlier cycle can be sequenced to obtain a greater number of potential devices. Having multiple devices is preferable as uncontrolled factors such as genetic context may affect the functioning of particular device sequences in vivo or in other applications.

Validation

Once a set of switch candidates are identified they can be synthesized individually from oligonucleotides in a manner similar to that described above for the initial library. These can then be tested individually using one cycle of the same method as shown in FIG. 1 as described above with the final output being the qPCR measured cleavage of the sequence in presence and absence of target. A dose-response curve of the device measuring cleavage under multiple target concentrations can also be so obtained.

In some uses of this method, the in vitro function is the desired outcome. In other applications, the aptamer contained within the functional devices can be extracted from the sequence, as it consists of one of the sequences that replaced a loop of the ribozyme. This aptamer can then be used in any other application requiring a molecular sensor. Note that for small molecule aptamers, this method has the unique strength that it can determine aptamers without requiring modification or immobilization of the target. In addition, the target need not even be explicitly identified as the aptamer found will differentially sense the two states used during the positive and negative selections.

Devices which function in vitro can also be transformed into the 3' untranslated region of a fluorescent reporter and transformed into cells. Effect of the device in the presence and absence of target can then be measured in vivo using flow cytometry or using other methods well-known in the field. Enriched pools can also be moved to in vivo methods prior to isolating specific sequences allowing final selections or a screen to be done under conditions that are closer to the conditions that will be used in application of an in vivo RNA device.

Modifications

Other modifications to the above method are possible, including: combination of the cotranscription and reverse transcription steps into a single step that concurrently performs both functions isothermally; combining the ligation step with prior step(s) allowing this step to be performed in the same mixture; combining all steps of one cycle of the method into a single step; and combining of the steps such that multiple cycles of enrichment can occur continuously in a single step.

In the description set forth above, an exemplary method for selectively prepending an additional sequence to desired cDNA molecules is described—that of ligating on a prefix oligonucleotide, e.g., using second splint oligonucleotide. This step may be implemented using a different method described below.

Figure 5:
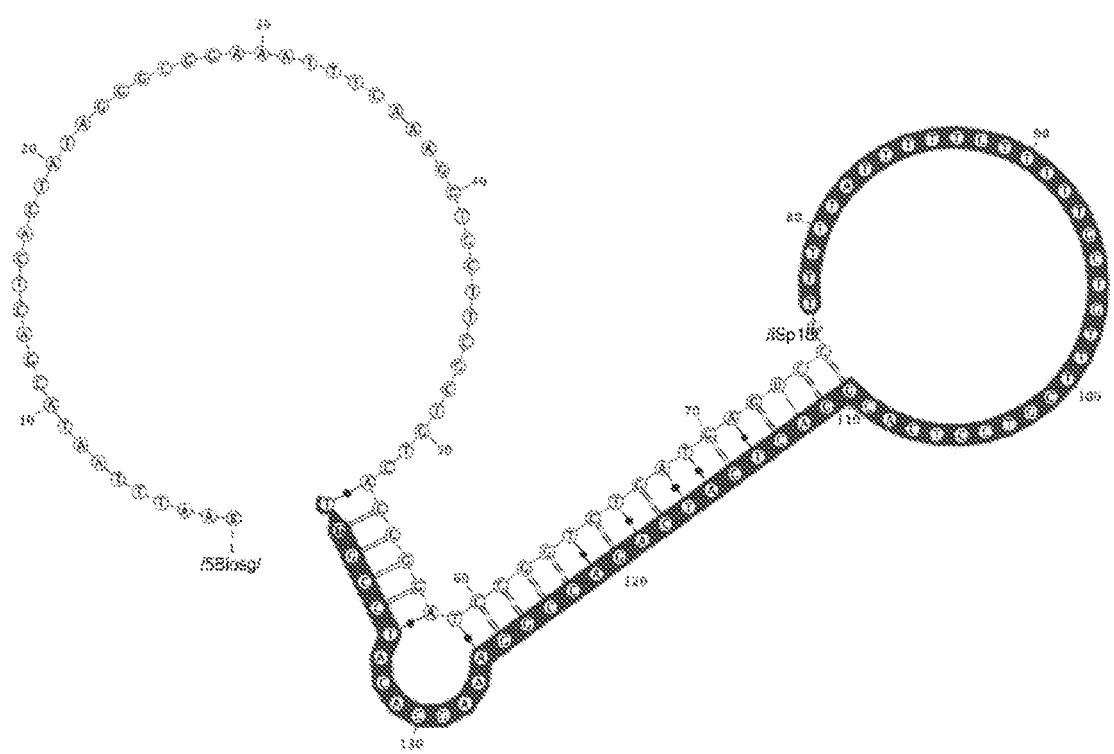
FIG. 5 shows a cDNA molecule following reverse transcription. Shaded nucleotides are parts of the cDNA that was complementary to the RNA. The reverse transcription primer consisted of nucleotides 1-105. Structure shown corresponds to a cleaved hammerhead ribozyme with loop1 sequence of UGUGCUU and loop2 sequence of GUGA. Ligation or extension can be used to add additional nucleotides to the 3' complementary to nucleotides up to nucleotide 52 above. The sequence depicted corresponds to SEQ ID NO:6.

A self-splinting configuration can be obtained by using a reverse transcription primer that has additional sequence on the 5' end of the oligonucleotide, i.e., a 5' tail sequence that does not hybridize to the RNA. The 3' end remains as described, performing the function of annealing to the RNA and acting as a primer for the reverse transcription reaction. Additional sequence on the 5' end is added which will be partially complementary to the cDNA molecule following reverse transcription. In addition, the primer may contain the reverse-complement of the sequence that will be ligated onto the 3'-end of the cDNA. Thus, the 5' tail of the reverse transcription primer can acts as the splint oligonucleotide previously described. In this way, no additional splint oligonucleotide is needed at the ligation step and, more importantly, the local concentration of the splint will be much higher since it is itself part of the same molecule to be splinted. The complementary sequence of this region to the cDNA also competes favorably with the secondary structure that is otherwise formed within the cDNA (the parts that correspond to the RNA hairpins themselves form hairpins which hamper the splint and ligation process). Thus the entire cDNA molecule becomes a long hairpin with a 5' overhang that is complementary to the oligonucleotide to be ligated. This configuration is illustrated in FIG. 5.

In addition, a similar 5' augmentation of the RT primer can also be used to extend the 3' end of the cDNA without ligating another oligonucleotide. In this variation, the 5' overhang is used a template for a DNA polymerase (e.g., Klenow exo-enzyme) to extend the 3' end of the cDNA resulting in the desired final sequence. This variation has the advantage that all of the DNA components of the reaction reside on a single molecule at high local concentration making the reaction very efficient.

With the above methods, the choice of whether to ligate/extend cleaved vs. uncleaved molecules is decided based on the sequence of the RT primer. For example, if the template molecules have prefix A and it is desired to extend only the cleaved molecules with a new prefix, B, then the RT primer contains a region complementary to the expected cDNA sequence up to the point where A and B diverge. After that, the RT primer sequence is complementary only to B. In this way, cDNA corresponding to uncleaved molecules will not have a 3' end complementary to the RT primer and will not be ligated or extended. Cleaved molecules will have a 3'-end complementary to the RT primer and can thus be extended to add B.

The prefix added above can also include a region containing a T7 promoter. In this way, the resulting extended or ligated cDNA molecule will have a double-stranded T7 promoter section and be in the correct configuration to allow T7 transcription of this DNA without further processing. Thus, the PCR step that would normally follow this step can be eliminated if desired (as mentioned on page 18, lines 10-12), or can be used to create additional copies of the desired molecules. These are shown in nucleotide positions 1-23 in FIGS. 5 and 6.

If the extended/transcribed molecule is used directly for T7 transcription, then it is possible that that transcription may continue past the desired endpoint of the RNA and transcribe the extended portion of the RT primer following the hairpin in the cDNA to its 5' end (which is the anti-sense T7 promoter). To prevent this, a spacer sequence, e.g., an 18-carbon spacer, can be inserted at the point where it is desired that RNA transcription terminate. This will result in an RNA molecule complementary to the sense-strand up to that spacer. The spacer is shown at position 76 in FIG. 5 and position 78 in FIG. 6.

Figure 6:
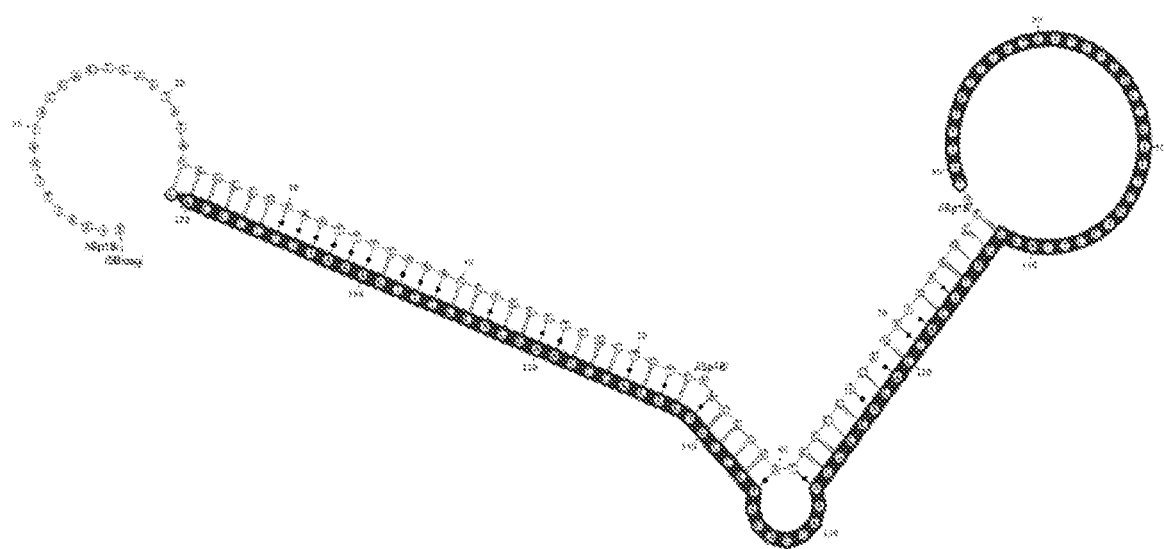
FIG. 6 shows another cDNA following reverse transcription. Shaded nucleotides are parts of the cDNA that was complementary to the RNA. The reverse transcription primer consisted of nucleotides 1-107. Structure shown corresponds to an uncleaved hammerhead ribozyme with loop1 sequence of UGUGCUU and loop2 sequence of GUGA. Ligation or extension can be used to add additional nucleotides to the 3' complementary to nucleotides up to nucleotide 23 above. Note that cDNA corresponding to cleaved RNA cannot be extended due to spacer at position 54. The sequence depicted corresponds to SEQ ID NO:7.

When it is desired to select only non-cleaving molecules, then the above methods can be modified such that the extended RT primer contain a region complementary to the X (A or B above) region which results in a 5' overhang of only the T7 promoter sequence. Thus, during extension or ligation the uncleaved molecules will have the T7 promoter regions prepended to the X region. To prevent the uncleaved molecules from also being extended, an additional spacer can be inserted in the RT primer sequence on the 5' side of the point where it would be complementary to the 3' end of the cDNA corresponding to the cleaved RNA. In this way, the 3' of the end would not be extended by polymerase due to the non-template spacers, nor would it be aligned correctly with a ligation oligonucleotide. Once the cDNA molecules corresponding to uncleaved RNA have the T7 promoter added, they can be used directly for T7 transcription or used as a template for subsequent PCR with the T7 region used as one of the primers. This concept is illustrated in FIG. 6.

In addition or alternative to the above, a uracil base (/dU/) may be present in the region of the hairpin loop that will be formed by the cDNA. This can be selectively cleaved through use of USER enzyme (NEB) separating the cDNA into two partially complementary strands. This cleavage allows higher efficiency of PCR or qPCR of the cDNA with primers that would otherwise be participating in a stem of the cDNA hairpin and thus less available for annealing to the primer. Following cleavage and heat denaturation (such as occurs during PCR), the strands would separate and compete only as another, low-concentration, intermolecular oligonucleotide rather than as a intramolecular competitor with a high local concentration. The/dU/position is shown in FIGS. 5 and 6.

In addition or alternative to the above, the reverse primer molecule may contain a 5' capture moiety such as a 5'-biotin group. Use of such a primer results in the cDNA containing that capture tag, e.g., 5'-biotin and thus allowing separation of the cDNA from other components of the mixture (such as RNA, prior round templates, etc.) using, e.g., streptavidin beads (e.g. Dynabeads C1 Streptavidin). In addition, if the cDNA is used directly as a T7 RNA polymerase template for the subsequent round, the resulting RNA can be separated from this template using magnetic separation, as briefly discussed above.

The sequencing methods can be improved using constricted libraries. At most points in the selection process, the library may contain many more unique molecules than can be sequenced. Since measurement of cleavage of particular sequences through sequencing requires multiple reads of the same sequence (followed by counting of the ratio of reads corresponding to cleaved and to uncleaved molecules), sequencing cannot be used to directly measure the cleavage statistics of even a subset of the members of such libraries. However, one can constrict the library by diluting it such that only a desired number of molecules are present. This constricted library can then be amplified by PCR to make many copies of each sequence, passed through the in vitro analytic process and then sequenced. As long as the number of sequencing reads per unique member of the constricted library is high, then the cleavage characteristics of those members can be measured and an estimate of the distribution of cleavages for the entire library can be formed.

Finally, to increase diversity of the library and increase the probability that a sequence with the desired properties is present in the library, mutagenesis of the pool can be performed. This is particularly advantageous to do during a pre-selection phase where the library is enriched for sequences that have high cleavage activity in the absence of any target molecules. During this stage, only a subset of the degenerate nucleotide positions are likely needed to achieve high cleavage. Thus, mutagenesis can add diversity to other regions without excessively undermining selection done in prior rounds to enrich cleavers.

Utility

A ligand-responsive ribozyme identified using the present method can be used in a variety of applications, such as modulating enzymatic activities, expression of non-coding RNAs and regulation, to ultimately engineer complex networks in mammalian or other organisms. A coding sequence for the ligand-responsive ribozyme can be incorporated into a variety of genes, and the ribozyme can then be used to control expression of a protein or a regulatory RNA involved in a variety of applications, such as gene control, signal transduction, metabolism, subcellular localization, and imaging applications, etc.

In one embodiment, the present ligand-responsive ribozyme can be used in imaging applications. In these embodiments, the aptamer may bind to a cellular metabolite, and binding of the aptamer to the metabolite in the cell modulates expression of a reporter protein (e.g., mCherry or GFP), thereby providing a non-invasive way to image the presence of the metabolite in vivo or in vitro. Alternatively, the present ligand-responsive ribozyme can be used to control metabolism or gene expression, e.g., by placing a coding sequence for the ribozyme into an expression cassette encoding an enzyme or transcription factor, for example. In this embodiment, addition of the ligand for the aptamer will change the expression of the enzyme or transcription factor. For example, the present ligand-responsive ribozyme can further be used to engineer novel regulatory pathways and control loops for applications in metabolic engineering (Khosla et al., Nat Rev Drug Discov 2, 1019-25 (2003)) and synthetic circuit design (Kobayashi et al., Proc Natl Acad Sci USA 101, 8414-9 (2004)) by enabling the cell to sense and respond to intracellular metabolite levels and environmental signals. Because the regulated nucleic acids' activity is tunable over a range of ligand concentrations, switches can be designed to inhibit or activate genes only when certain metabolites exceed or go below certain concentrations. Balancing heterologous gene expression in biosynthetic pathways (Berens et al., Bioorg Med Chem 9, 2549-56 (2001)) to maximize product yield can be achieved with aptamer-regulated nucleic acids that regulate expression of biosynthetic genes in response to pathway intermediate levels. Synthetic gene circuits have recently been used to understand and model cellular networks (Nagai et al., Nat Biotechnol 20, 87-90 (2002)) and to achieve cellular control as a step towards programmable cell behavior (Watkins et al., Curr Opin Mol Ther 4, 224-8 (2002)). Gene circuits can be built using combinations of aptamer-regulated nucleic acids as regulators for precise control schemes. Aptamer-regulated nucleic acids will be useful tools in building and characterizing circuits that accurately model natural regulatory pathways and yield further insight into these prevalent regulation schemes.

In some embodiments, the present ligand-responsive ribozyme can be used to increase or decrease expression of a guide RNA in a ligand-dependent manner, thereby allowing one to make changes to a genome in a ligand-dependent manner. In some embodiments, the aptamer determined using this method can be used for other applications independent of ribozymes, such as for binding or inhibition of targets.

What is claimed is:

1. A method of adding additional sequence to the 3' end of a cDNA comprising:
   (a) obtaining a reverse transcription primer which has a 3' end that is complementary to the RNA to be transcribed, an additional region complementary to the 3' end of the cDNA, and a template sequence;
   (b) reverse transcribing the RNA using the reverse transcription primer of (a) to produce cDNA molecules that comprises the additional region of (a) and the template sequence of (a),
   (c) allowing the 3' end of the cDNA molecules of step (b) to intramolecularly anneal to the additional region; and
   (d) adding a sequence of nucleotides to the 3' end of the cDNA using the template sequence as a template.

2. The method of claim 1, where step (d) is done by a DNA polymerase.

3. The method of claim 1, where step (d) is done by ligation.

4. The method of claim 1, where the reverse-transcription primer also contains a spacer.

5. The method of claim 1, where the reverse-transcription primer also contains a biotin modification.

6. A method for selectively ligating a prefix oligonucleotide to cDNA, comprising:
   performing reverse transcription in the presence of a reverse transcription primer that is partially complementary to multiple sequence regions, including a) the RNA, b) the cDNA that will be formed, and c) the prefix sequence,
   allowing the cDNA to fold into a conformation such that region b) at least partially hybridizes with another part of the cDNA,
   combining the prefix oligonucleotide to be ligated with the cDNA addition of a ligase to produce a ligation mix; and,
   incubating the ligation mix to ligate the prefix oligonucleotide to the cDNA.

7. A method for selectively prepending a prefix sequence of nucleotides to cDNA, comprising:
   performing reverse transcription in the presence of a reverse transcription primer that is partially complementary to multiple sequence regions, including a) the RNA, b) the cDNA that will be formed, and c) the prefix oligonucleotide,
   allowing the cDNA to fold into a conformation such that region b) at least partially hybridizes with another part of the cDNA,
   addition of a DNA polymerase to produce a synthesis mix; and,
   incubating the synthesis mix to extend the cDNA with the prefix sequence.

* * * * *